2 Sheets—Sheet 1.

I. L. PULVERMACHER.

ELECTRO-GALVANIC CHAINS, BANDS, &c.

Reissued July 4, 1876.

No. 7,207.

Witnesses:

Donn P. Turtchell.

Hill W. Dodge.

Inventor:

I. L. Pulvermacher by Dodge & Son

Attys.

N. PETERS, PHOTO-LITHOGRAPHER, WASHINGTON, D. C.

I. L. PULVERMACHER.

ELECTRO-GALVANIC CHAINS, BANDS, &c.

No. 7,207. Reissued July 4, 1876.

Witnesses:

Donn F. Quitchell.

Will H. Dodge.

Inventor:

I. L. Pulvermacher.

by Dodger & Son

Attys.

N. PETERS, PHOTO-LITHOGRAPHER, WASHINGTON, D. C.

UNITED STATES PATENT OFFICE.

ISAAC LOUIS PULVERMACHER, OF LONDON, ENGLAND, ASSIGNOR TO JOHN E. HETHERINGTON, OF CINCINNATI, OHIO.

IMPROVEMENT IN ELECTRO-GALVANIC CHAINS, BANDS, &c.

Specification forming part of Letters Patent No. 120,772, dated November 7, 1871; reissue No. 7,207, dated July 4, 1876; application filed April 28, 1876.

DIVISION A.

*To all whom it may concern:*

Be it known that I, ISAAC LOUIS PULVERMACHER, of London, England, have invented certain new and useful Improvements in Electro-Galvanic Chains, Bands, &c.; and I do hereby declare that the following is a full, clear, and exact description thereof, reference being had to the accompanying drawings, making part of this specification, and to the letters of reference marked thereon—like letters indicating like parts wherever they occur.

To enable others skilled in the art to construct and use my invention, I will proceed to describe it.

My invention consists, first, in making chain batteries, as hereafter described, so that the zinc may be securely held, and when consumed readily replaced without detaching the chain, or injuring the elements composing the same.

Figure 1:
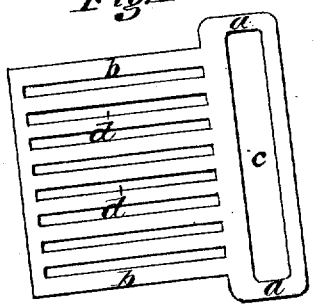
Figure 2:
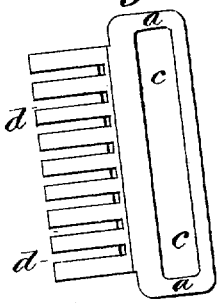
Figure 3:
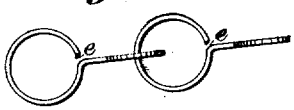
Figure 6:
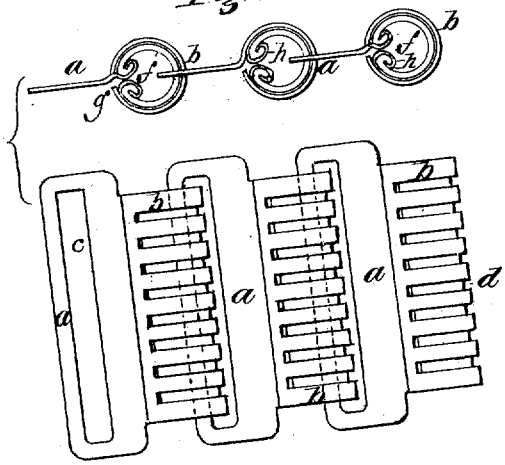

Each link or portion of the chain is formed from a copper plate, as represented at Figure 1 of the accompanying drawings, one-fourth or thereabout, marked *a*, being of greater width than the other three-fourths, marked *b*. This wider portion *a* has a longitudinal slot, *c*, therein, so that it forms a kind of buckle, and the other portion has a series of narrow slots, *d*, at right angles to the slot *c*. The narrower portion *b* is then bent round cylindrically into the form of a tube, as shown in Figs. 2 and 3. To connect the links thus made in order to form a chain, the buckle *a* of one link is introduced into the tube *b* of the next link, as shown in Fig. 3, through the slit *e*, which exists in this other tube. This slit *e*, except when the buckle is being introduced, remains closed, owing to the elasticity of the tube. To convert the copper chain thus formed of links into a volta-electric chain, I introduce into each copper tube *b* a zinc tube, *f*, as represented in Fig. 6, with a longitudinal slit, *g*, made, as hereafter described.

Figure 4:
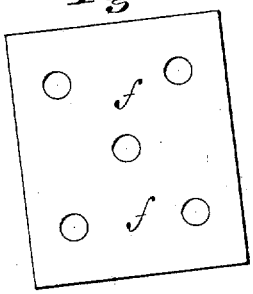
Figure 5:
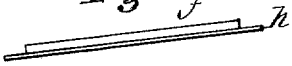

To maintain perfect insulation and regular voltaic contact, I make the zinc tubes as follows: I make a perforated zinc plate, as shown in Fig. 4, a little wider than the narrower portion *b* of the copper plate, from which the copper tube has been formed, and I cover one side with any suitable fabric, *h*, as shown in edge view in Fig. 5, which fabric extends beyond the opposite edges of the plate *f*, and is doubled and pasted or gummed down over upon the opposite side. I then double over these edges so that the fabric is held thereby. I next bend the zinc plate cylindrically into the form of a tube, that side which is covered with fabric being outermost, as seen in Fig. 6. The buckle *a* of the link, next adjoining that in which the zinc tube *f* is inserted, is made to slide into the slit *g* of the zinc tube, and the slits of the copper and zinc tubes are then brought opposite each other, or nearly so, as seen in Fig. 6. After the zinc tube *f* has been inserted into the copper tube *a*, I make it steady therein, in order to prevent false contacts, by inserting a conical mandrel or tool. This tool expands both tubes; but the zinc tube, being non-elastic, retains its expanded form when the tool is withdrawn, while the copper tube, being elastic, presses upon and steadies the zinc tube. The voltaic electric chain thus formed is drawn through any dilute acid, which penetrates through the slots *d* of the copper tube *b*, and the perforations in the zinc tube *f*, and by the alternate contact of the copper buckle *a* of one element or link with the bare inside zinc tube *f* of the next element or link, electricity is produced of a tension proportionate to the number of links in the chain.

In the arrangement before described, magnesium may be conveniently substituted for zinc.

Figure 7:
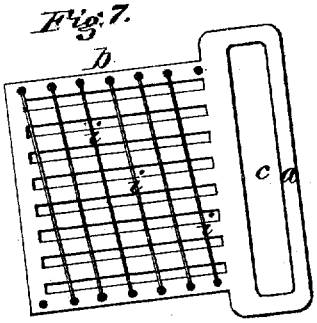

Sometimes I dispense with the fabric *h* on the zinc tube and use instead thereof thread, as shown at *i*, Fig. 7. This thread is laced to and through apertures in the copper tube *b*, and prevents contact of this tube and the zinc tube *f*, and has the additional advantage of facilitating the flow of the acid.

Figure 8:
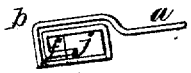

Sometimes, also, instead of bending the copper *b* into the form of a tube, I bend it in the form represented in Fig. 8, and I bend the zinc plate *f* into a corresponding form, as shown in the same figure, one end of this plate being less bent in than the other, in order that it may come flush with the edge of the copper.

Figure 9:
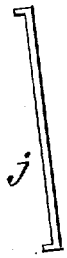

To prevent the zinc *f* becoming detached from the copper *b*, I use a piece of ebonite or other hard insulating material, of the shape represented at *j*, Fig. 9. This piece is pushed down inside the zinc *f*, as shown in Fig. 8, and the enlarged ends of the piece *j*, by fitting over the zinc and copper, prevent the zinc coming out.

Figure 10:
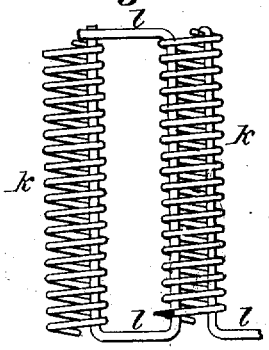
Figure 11:
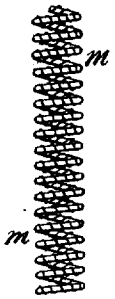

A modification of the chain before described consists in connecting lengths of copper spirals to each other by means of copper wire bent into rectangular form, as shown in Fig. 10, in which *k k* are copper spirals, connected by a copper wire, *l*, bent into rectangular form. The two longer sides of the rectangle are passed through the spirals, and the ends of the wire, from which the rectangle is formed, are bent into the form of hooks, as shown, to enable them to be attached to each other. A zinc spiral, *m*, Fig. 11, is introduced into each copper spiral *k*, and, to prevent metallic contact of the copper and zinc spirals, either of them may have cotton or other thread wound thereon.

Figure 12:
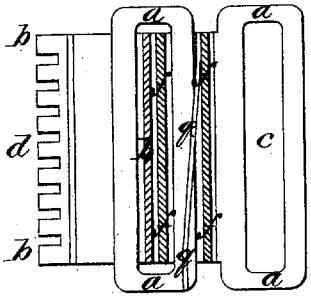

Open zinc cylinders, as hereinbefore described, may be employed, instead of the zinc spirals. When zinc and copper cylinders are used in order to secure inoxidizable voltaic contact between the zinc of one link and the copper of the next adjoining link, I solder one end of a thin flat copper wire, *q*, Fig. 12, placed inside the copper tube *b*, to one end of the zinc tube *f*, and I solder the other end to the opposite end of the copper *a* of the next adjoining link, as shown. Sometimes I employ two such wires between the zinc tube of every link and the copper of the link next adjoining, these two wires being soldered in opposite ways.

Figure 13:
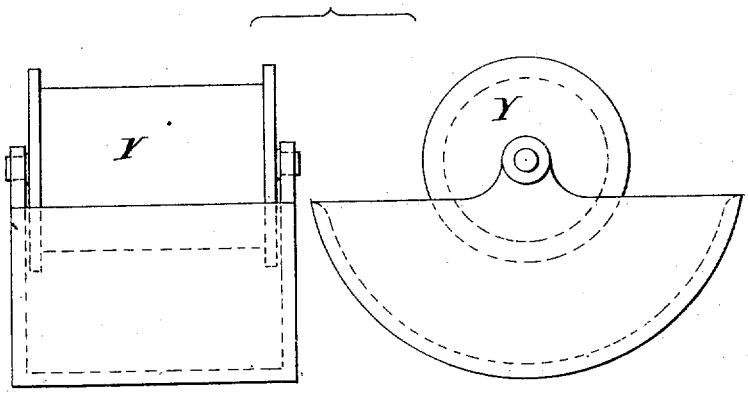

There are many ways in which the bands, when made up, may be charged, one of which is shown in Fig. 13, in which Y represents a roller mounted in a trough or bowl. This trough or bowl is supplied with exciting liquid, and the band or belt is passed around and under the roller Y, being thus immersed in the liquid; or, instead of this, the band or belt may be dipped directly into the liquid.

Having thus described my invention, what I claim is—

1. A galvano-electric chain or band, constructed and operating substantially as herein described.

2. The combination of the slotted plates *o* and the plates *f* with the insulating fabric or threads, all arranged to operate substantially as shown and described.

3. The cylinder Y, mounted in the trough, substantially as described, for charging the bands or chains, as set forth.

ISAAC LOUIS PULVERMACHER.

Witnesses:

E. N. DANIEL,
166 *Fleet Street, London.*

J. S. ROBINS,
2 *Waterloo Place, Pall Mall, London.*